(12) United States Patent
Lastovich

(10) Patent No.: US 6,899,838 B2
(45) Date of Patent: May 31, 2005

(54) METHOD OF FORMING A MOLD AND MOLDING A MICRO-DEVICE

(75) Inventor: Alexander G. Lastovich, Raleigh, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 239 days.

(21) Appl. No.: 10/193,317

(22) Filed: Jul. 12, 2002

(65) Prior Publication Data

US 2004/0007796 A1 Jan. 15, 2004

(51) Int. Cl.[7] .......................... B29C 33/38; B29C 45/00
(52) U.S. Cl. ...................... 264/102; 264/156; 264/220; 264/225; 264/317; 419/38
(58) Field of Search ................................. 264/317, 156, 264/102, 220, 225; 419/38, 1; 205/70

(56) References Cited

U.S. PATENT DOCUMENTS

| | | | |
|---|---|---|---|
| 4,262,875 A | * 4/1981 | Nyman et al. | ........... 249/114.1 |
| 4,661,212 A | * 4/1987 | Ehrfeld et al. | ................ 205/75 |
| 5,071,597 A | * 12/1991 | D'Amato et al. | .......... 264/1.34 |
| 5,073,237 A | * 12/1991 | Bacher et al. | .............. 264/320 |
| 5,436,764 A | * 7/1995 | Umetani et al. | ............. 259/566 |
| 5,501,784 A | 3/1996 | Lessmollmann et al. | |
| 5,658,515 A | 8/1997 | Lee et al. | |
| 5,793,519 A | * 8/1998 | Furlani et al. | .............. 359/291 |
| 6,187,210 B1 | 2/2001 | Lebouitz et al. | |
| 6,256,533 B1 | 7/2001 | Yuzhakov et al. | |
| 6,312,612 B1 | 11/2001 | Sherman et al. | |
| 6,331,266 B1 | 12/2001 | Powell et al. | |
| 6,334,856 B1 | 1/2002 | Allen et al. | |
| 6,379,592 B1 | * 4/2002 | Lundin et al. | ............. 264/1.24 |
| 6,610,235 B1 | 8/2003 | Pisano et al. | |
| 6,679,471 B2 | * 1/2004 | Domeier et al. | .............. 249/60 |
| 6,692,680 B2 | * 2/2004 | Lee et al. | .................... 264/485 |
| 2002/0020688 A1 | 2/2002 | Sherman et al. | |

FOREIGN PATENT DOCUMENTS

| | | |
|---|---|---|
| EP | 0 437 345 A2 | 7/1991 |
| EP | 0 844 056 A1 | 5/1998 |
| EP | 1 088 642 A1 | 4/2001 |
| WO | WO 00/74764 A1 | 12/2000 |
| WO | WO 00/74764 | * 12/2000 |
| WO | WO 01/36036 | 5/2001 |

* cited by examiner

*Primary Examiner*—Allan R. Kuhns
(74) *Attorney, Agent, or Firm*—Robert E. West

(57) ABSTRACT

A method of forming a device including a plurality of micron or sub-micron sized features is provided. A master having a surface contour defining a plurality of features is provided. The surface contour of the master is coated with at least one layer of material to form a shell. The master is removed from the shell to form a negative image of the surface contour in the shell. The negative image in the shell is filled with material, for example, polycarbonate, polyacrylic, or polystyrene, to form a device having features substantially the same as the master. The negative image may be filled using injection molding, compression molding, embossing or any other compatible technique.

39 Claims, 6 Drawing Sheets

METHOD OF FORMING A MOLD AND MOLDING A MICRO-DEVICE

FIELD OF THE INVENTION

The present invention relates to a method of manufacturing a device, and particularly, a micro-device. More particularly, the invention is directed to a method of forming a mold for a micro-device and molding a micro-device for medical use.

BACKGROUND OF THE INVENTION

There has been an increase in interest in processes for the manufacture of small devices in the field of biological and biochemical analysis. The manufacture of devices used for analytical testing uses techniques similar to those used in the electronics industry. Examples of these manufacturing techniques include photolithography and wet chemical etching. The devices are often made from solid substrates such as silicon and glass.

Microanalytical devices have been used for performing various analytical reactions. For example, U.S. Pat. No. 5,498,392 to Wilding et al. discloses a mesoscale device having microfabricated fluid channels and chambers in a solid substrate for the performance of nucleic acid amplification reactions. U.S. Pat. No. 5,304,487 to Wilding et al. discloses a mesoscale device having a cell handling region for detecting an analyte in a sample. The microchannels and chambers have a cross-sectional dimension ranging from 0.1 micron to 500 microns. U.S. Pat. No. 5,885,470 to Parce et al. discloses a microfluidic transport device made from a polymeric substrate having fluid channels that can be a few microns wide.

There has also been an increased interest in microneedle injection for the transdermal delivery of various drugs. The microneedle devices can have a plurality of microneedles with a length of a few hundred microns. One example of a microneedle device for delivering a drug to a patient is disclosed in U.S. Pat. No. 5,879,326 to Godshall et al. Microneedle drug delivery devices are able to penetrate the stratum corneum of the skin with less irritation. The stratum corneum is a complex structure of compacted keratinized cell remnants having a thickness of about 10–30 microns and forms a waterproof membrane to protect the body from invasion by various substances and the outward migration of various compounds. The delivery of drugs through the skin is enhanced by either increasing the permeability of the skin or increasing the force or energy used to direct the drugs through the skin.

One method of delivering drugs through the skin is by forming micropores or cuts through the stratum corneum. By penetrating the stratum corneum and delivering the drug to the skin in or below the stratum corneum, many drugs can be effectively administered. The devices for penetrating the stratum corneum generally include a plurality of micron size needles or blades having a length to penetrate the stratum corneum without passing completely through the epidermis. Examples of these devices are disclosed in U.S. Pat. No. 5,879,326 to Godshall et al.; U.S. Pat. No. 5,250,023 to Lee et al.; and WO 97/48440.

These devices are usually made from silicon or other metals using etching methods. For example, U.S. Pat. No. 6,312,612 to Sherman describes a method of forming a microneedle array using MEMS technology and standard microfabrication techniques. Although effective, the resulting microneedle devices are expensive to manufacture and are difficult to produce in large numbers. Thus, there have been recent efforts to form micro-devices from polymers.

The '612 patent to Sherman also describes a method of forming micro-devices from a polymer. A mold base having a number of micropillars extending therefrom is formed by microelectrode-discharge machining or by photolithographic processing. A thin layer of polymer is arranged on top of the micropillars. The layer of polymer is heated so it deforms around the micropillars, forming micro-devices. The microelectrode-discharge machining or photolithographic processing used to form the mold are time consuming and expensive processes.

U.S. Pat. No. 6,331,266 to Powell et al. describes a process to form a molded micro-device from polymers. In particular Powell et al. describe a method for forming a micro-device from plastic by injection molding, compression molding, or embossing. The method of Powell et al. focuses on forming the micro-device from a mold, and not the creation of the mold itself.

U.S. Pat. No. 5,250,023 to Lee et al. describes a polymer micromold and fabrication process for the mold. A mold assembly with micro-sized features is formed. The mold assembly has a hollow portion that is fabricated from a sacrificial mandrel. The mandrel is surface-treated and coated to form an outer shell. The mandrel is then etched away leaving the outer shell as the mold. The process described in Lee et al. can only produce a singular hollow mold at a time. The mold created is used in conjunction with polymer extrusion in which polymer is passed through the hollow mold.

The prior methods and apparatus for the manufacture of micro-devices for medical use have exhibited some success but are generally time consuming and expensive. For example, the process of Lee et al. can only form a mold for a singular device. Accordingly, a continuing need exists in the industry for an improved method for the manufacture of micro-devices.

SUMMARY OF THE INVENTION

The present invention is directed to a method of manufacturing devices, such as, micro-devices for medical and other uses. The method and apparatus of the invention are suitable for molding plastic devices having micron and submicron features. The medical micro-devices are devices having channels, needles, points or other structural features having dimensions ranging from less than 1 micron to several hundred microns in length or width. Examples of micro-devices that can be molded in accordance with the present invention include analytical microchannel devices, microneedles, pipettes and the like. Analytical microchannel devices, for example, can include microchannels having a diameter ranging from about 0.5 microns to about 500 microns.

In one embodiment of the invention, the micro-device is used for penetrating or abrading the stratum corneum of the skin and for the transdermal delivery of a substance, such as a drug or pharmaceutical agent, through the abraded area. The device includes a plurality of microprotrusions for abrading and preparing a delivery site on the skin to enhance the delivery of a substance through the stratum corneum of the skin to a sufficient depth where the substance can be absorbed and utilized by the body.

According to an exemplary embodiment of the invention, a method of forming a mold for a micro-device including an array of micro-features is provided. A master or original micro-device having a surface contour is provided. The surface contour of the master is coated with a layer of material, the layer preferably having a thickness of at least about 0.01–0.2 inches and preferably 0.07 inches or greater. The master is removed from the layer of material to form a negative image of the master in the layer of material. The negative image may then be used in a molding process to form a positive image having features that are substantially the same as the features of the master.

In one embodiment of the invention, the master is sacrificed when it is removed from the layer of material. For example, the master may be removed by etching. In another embodiment, the master is coated with a release layer, before being coated with the layer of material. The release layer facilitates removal of the master from the negative image, preserving the master unharmed.

According to another embodiment of the invention, a method of forming a device including a plurality of micron or sub-micron sized features is provided. A master having a surface contour defining a plurality of features is provided. The surface contour of the master is coated with at least one layer of material to form a shell. The master is removed from the shell to form a negative image of the surface contour in the shell. The negative image in the shell is substantially filled with material, for example, polycarbonate, acrylic (cyro 1–40) LCP, cyclic olefinic copolymers (COC), polystyrene, or other suitable structural plastic, to form a device having features substantially the same as the master. Of course, other types of materials may be used to fill the shell. The negative image may be filled using injection molding, compression molding, embossing or any other compatible technique.

In a further embodiment, the shell defines recesses having a depth of about 5 microns to about 250 microns. The recesses may be arranged in an array of uniformly spaced or non-uniformly spaced rows and columns or other patterns, including random patterns, to provide a density of about 1 to about 100 of the recess per $mm^2$. The shell is a negative or reverse image for molding the features of the master, where the master can have recesses or peaks on its surface contour ranging from about 0.5 micron to several hundred microns in length.

The advantages and other salient features of the invention will become apparent from the following detailed description which, taken in conjunction with the annexed drawings, discloses preferred embodiments of the invention.

BRIEF DESCRIPTION OF THE DRAWINGS

The following is a brief description of the drawings, in which.

DETAILED DESCRIPTION OF THE PREFERRED EMBODIMENT

Figure 1:
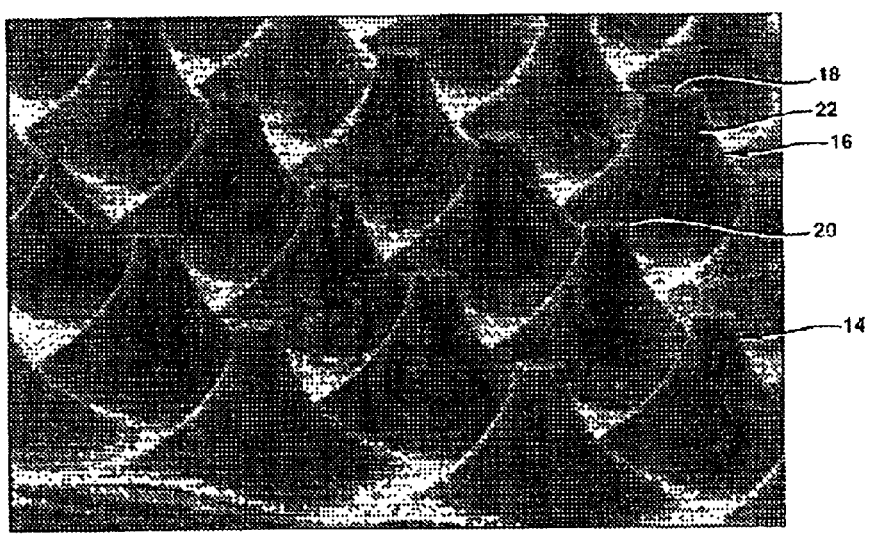
FIG. 1 is a perspective view of a microabrader surface one the embodiment of the invention.

The present invention is directed to a method of manufacturing a micro-device, such as a medical device, having a plurality of micron or submicron size features. In one embodiment the micro-device is a microabrader device for preparing the skin for transdermally administering a substance to a patient or withdrawing a substance from the body of a patient. The method of this embodiment is able to form a mold for a device having a plurality of micron size features, such as a microabrader device. The device is molded from a polymeric material. The molding method, such as injection molding, is able to produce a high volume of the devices with micron or submicron size features in an inexpensive manner and with a high degree of consistency. The mold is able to withstand repeated use and the high pressures of the molding process.

The molds formed by the method of the invention are preferably used to mold devices that have micron or submicron size details integrally molded therein. Examples of micro-devices that can be molded by the method of the invention include medical and analytical devices having micron size channels, conduits or capillaries, surgical needles, prosthetic devices, implants and the like. The method and molding apparatus are particularly suitable for the molded medical devices having channels, recesses, needles, protrusions or other structural elements having at least one dimension ranging from about 0.5 micron to about 500 microns. The illustrated embodiment relates to a microprotrusion device for abrading the skin, although it will be understood that the invention is not limited to microabrader or microprotrusion devices and can be used to mold a variety of devices.

The microabrader devices made by the method of the present invention are particularly suitable for use in preparing skin for administering a pharmaceutical agent to a patient or withdrawing a substance intradermally from a patient. As used herein, a pharmaceutical agent includes a substance having biological activity such as antibiotics, antiviral agents, analgesics, anesthetics, anorexics, antiarthritics, antidepressants, antihistamines, anti-inflammatory agents, antineoplastic agents, vaccines (including DNA vaccines), and the like. Other substances that can be delivered intradermally to a patient include naturally occurring, synthesized or recombinantly produced proteins, peptides and fragments thereof. Substances and agents withdrawn from the body include analytes, drugs, glucose, body electrolytes, alcohol, blood gases, and the like. The above substances are not meant to be an exhaustive list and other substances suitable for delivery or withdrawal will be apparent to those skilled in the art.

In one embodiment of the invention, the method is directed to the manufacture of a microabrader for preparing the skin, and particularly the stratum corneum, for enhancing the delivery of a substance transdermally to a patient or for sampling various agents from the patient. The microabrader device is moved or rubbed on the skin to abrade and remove at least a portion of the stratum corneum. An active or passive drug delivery device or sampling device as known in the art is applied over the abraded area. As used herein, the term microabrader refers to a device that can abrade the skin to increase the permeability of the skin without causing unacceptable skin irritation or compromising the skin barrier to infectious agents.

Figure 2:
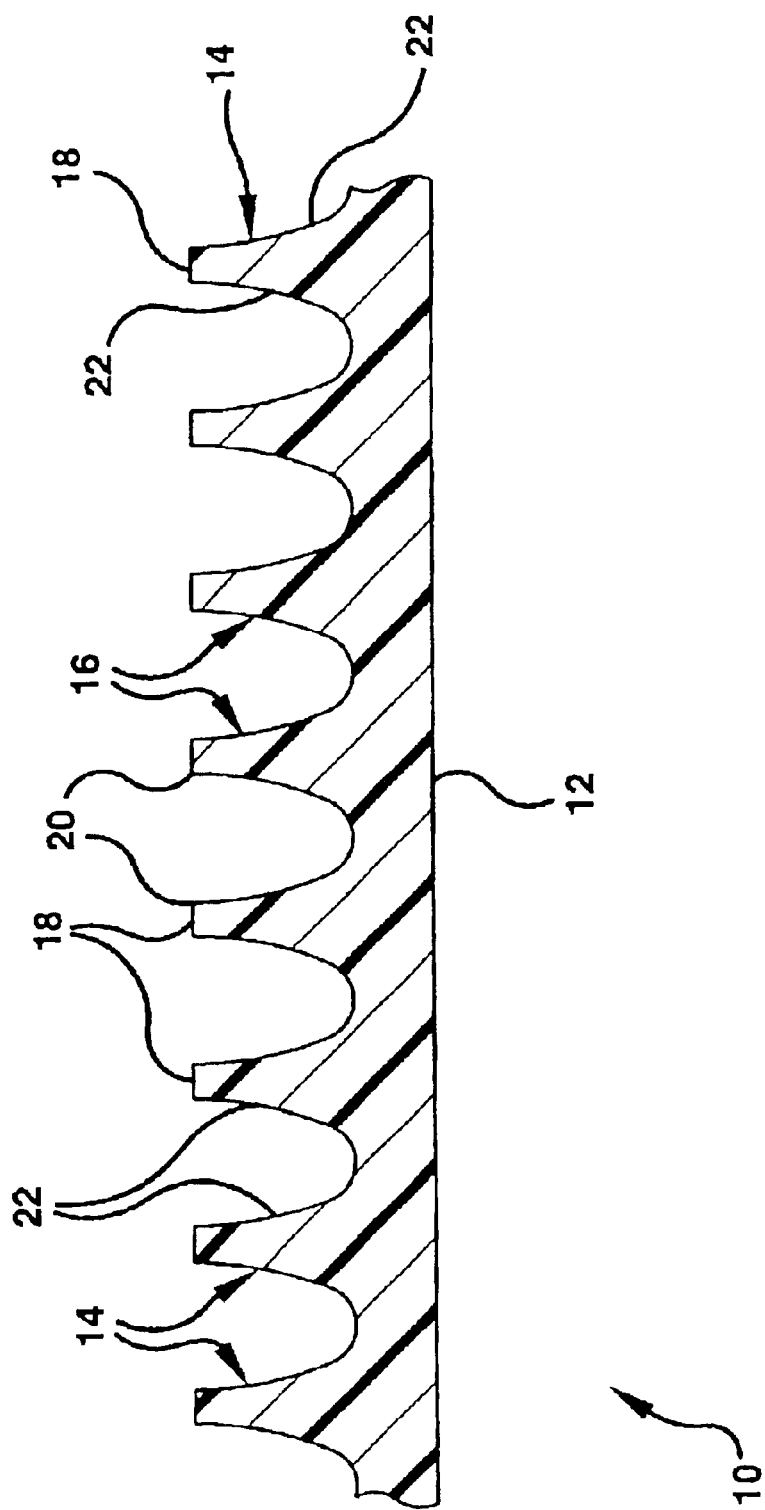
FIG. 2 is a partial cross-sectional view of the microabrader.

In the illustrated embodiment shown in FIGS. 1 and 2, the microabrader device 10 made by a method according to an embodiment of the present invention includes a substantially planar body or support 12 having a plurality of micropro-trusions 14 extending from the bottom surface of the support. The dimensions of the support 12 can vary depending on the length of the microprotrusions, the number of microprotrusions in a given area and the amount of the substance to be administered to the patient. Typically, the support 12 has a surface area of about 1–4 square centimeters (cm²). In preferred embodiments, the support surface 12 has a surface area of about 2 cm².

Figure 3:
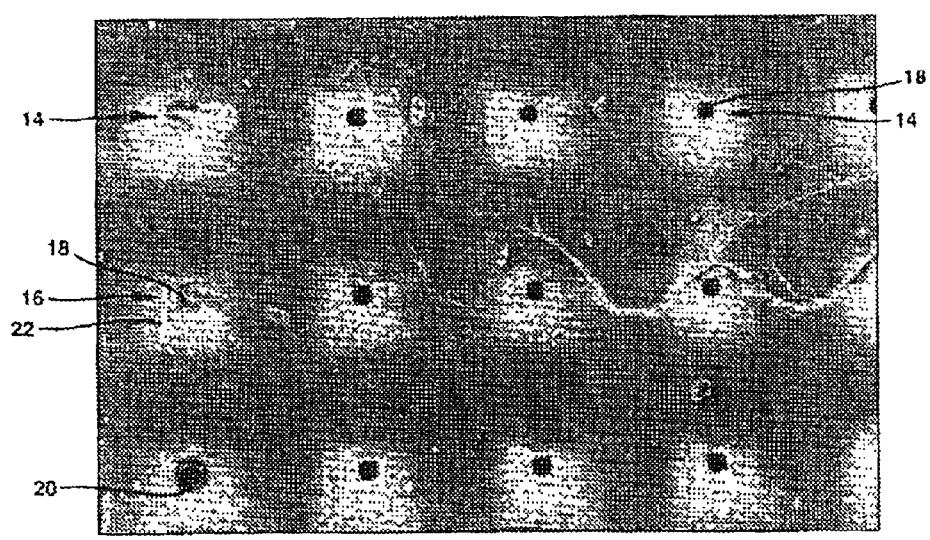
FIG. 3 is a top view of the microabrader in the embodiment of FIG. 1 showing the tips of the microprotrusions.

As shown in FIGS. 1 and 2, the microprotrusions 14 are integrally formed and attached to the surface of the support 12 and extend substantially perpendicular to the plane of the support 12. The microprotrusions 14 in the illustrated embodiment are arranged in a plurality of rows and columns and are substantially spaced apart a uniform distance. The microprotrusions 14 in this embodiment have a generally pyramidal shape with sides 16 extending to a tip 18. The sides 16 as shown have a generally concave surface when viewed in cross-section and form a curved surface extending from the support 12 to the tip 18. In the embodiment illustrated, the microprotrusions are formed by four sides 16 of substantially equal shape and dimension. As shown in FIGS. 2 and 3, each of the sides 16 of the microprotrusions 14 have opposite side edges contiguous with an adjacent side and form a scraping edge 22 extending outward from the support 12. The scraping edges 22 define a generally triangular or trapezoidal scraping surface corresponding to the shape of the side 16. In further embodiments, the microprotrusions 14 can be formed with fewer or more sides. Alternatively, the microprotrusions can be conical or cylindrical, with conical or pointed tips. Additionally, the microprotrusions can be arranged on the support 12 in a non-uniform manner.

The microprotrusions 14 shown terminate at blunt tips 18. Generally, the tips 18 are substantially flat and parallel to the support 14. Each tip 18 preferably forms a well defined, sharp edge 20 where it meets the sides 16. The edge 20 extends substantially parallel to the support 12 and defines a scraping edge. In further embodiments, the edge 20 can be slightly rounded to form a smooth transition from the sides 16 to the tip 18.

The micro-devices, such as the microabrader device 10 and the microprotrusions 14 can be made from a plastic material that is preferably non-reactive with the substance being administered and that can be used in various molding processes, and particularly injection molding. Suitable plastic materials include, for example, polyethylene, polypropylene, acrylic, cyclic olefinic copolymers (COC), polyamides, polystyrenes, polyesters and polycarbonates, filled or un-filled and copolymers thereof as known in the art. Preferred polymers include COC and an acrylic available from CYRO under the trade name L40. The length and thickness of the microprotrusions are selected based on the particular substance being administered and the thickness of the stratum corneum in the location where the device is to be applied. The microprotrusions can have a length of about 5 microns up to about 250 microns. The microprotrusions in the illustrated embodiment have a generally pyramidal shape and are perpendicular to the plane of the device. The microprotrusions can be solid or hollow members.

As shown in FIGS. 2 and 3, the microprotrusions 14 for microabrader 10 are typically spaced apart uniformly in rows and columns to form an array. Typically, the rows of microprotrusions are spaced in rows to provide a density of about 1 to about 10 per millimeter (mm) and provide a needle density of about 1 to about 100 needles per mm², although the molding method of the described embodiment enables the spacing to be varied as needed.

In one embodiment, the micro-devices of the invention are manufactured by injection molding. An injection molding process for micro-devices is described in U.S. Pat. No. 6,331,266 to Powell et al. and is incorporated herein by reference. The molding method described in Powell et al. uses a mold member having a positive image of the device being manufactured. The mold member is filled with a polymeric material to form a reverse or negative image of the micro-device. The method of forming mold member having a negative image according to the present invention can be combined with the injection molding process described in Powell et al. to form high quality micro-devices in an efficient manner.

In order to form the negative or reverse image used in the molding process, a positive image is first needed. A master, for example an original of a micro-device, provides the positive image. The master is essentially an example of the desired finished product. For example, the master in the described embodiment is microabrader 10. As shown in FIGS. 1 and 2, the microabrader 10 has a surface contour that defines its features, such as the microprotrusions 14. The surface contour of the microabrader 10 is preferably a contour of an outer or exterior surface. In general, the master can have any shape or geometry. The microabrader 10 used as a master is typically made from silicon. The master microabrader can be made using techniques used to shape and form silicon surfaces, for example, photolithography and wet etching methods that are substantially the same as known by those skilled in the art for producing electronic components. The silicon microabrader can also be made using various micromachining processes that typically use a micron-size diamond milling machine.

Additionally, techniques are provided for forming devices that are not easily formed in silicon. A pattern that is not easily formed in silicon to provide for edges arranged in un-symmetric patterns may be formed by dividing patterns that are easy to form in silicon into several sections. These sections are placed together, such as glued together, to form the desired pattern. For example, it is not easy to etch a rotational pattern in which the edges of the protrusions are arranged to substantially face in a circular pattern in silicon due to the crystal lattice structure of the silicon. To overcome this limitation, the rotational structure may be formed in sections, similar to pieces of a pie, that are glued together to form the complete rotational pattern. This complete pattern can then be used as the positive image. Thus, it is possible to form a complete plastic version of a pattern that cannot be formed complete in silicon. Other examples include circular rings of protrusions arranged in tiers of varying heights from a base, among others.

In order to form the negative image of the master, here microabrader 10, the surface contour of the microabrader 10 is covered with at least one layer of material. The layer of material preferably does not cover interior surfaces of the microabrader. Although in some instances this may be desirable. The layer of material creates a shell defining the negative image of the microabrader 10. The layer of material can be provided over the outer surface contour of the microabrader 10 via a plating process. The layer of material may be formed from any metallic or other suitable material. However, nickel is preferable since it has a similar coefficient of expansion to that of steel which makes it easy to use at the elevated temperatures present in molding applications. When the layer of material comprises nickel, it may be deposited over the master using Nickel Composite Tooling (NCT), a plating technique. NCT is a trade name for a commercial process available from Vintage Industries.

In another embodiment of the invention, the layer of material can be provided over the outer surface contour of the microabrader 10 via a sintering process. The master is coated with a powdered metallic material, for example by immersing the master in the powdered material. The powdered material is then sintered to form the shell.

The shell is preferably formed at least about 0.01–0.2 inches thick and preferably about 0.07 inches or greater. A thick shell provides a more robust negative image that can withstand the high pressures generated during the subsequent molding process. A thick shell also produces a mold with a longer working life. Additionally, the thickness of the shell is chosen such that the back of the shell can be machined to provide a generally flat surface to mate with the cavity of the mold thus eliminating the need to epoxy the shell into the mold.

After the layer of nickel or other material is applied to the master, the master is removed from the layer of material leaving a negative image of the master in the nickel shell. There are several different ways in which the master can be removed from the nickel layer. For example, the master can be removed by etching, in which case the master is sacrificed during removal. Alternatively, the master can be coated so that the master releases from the shell substantially intact. The master can then be used to create other negative images. For example, in a master with no undercut, the mold cavity off the first master can be plated (for example, electroforming or electroless-forming) to make a metal master Multiple molds may then be created off this new master allowing multiple cavities off the same silicon chip.

In some instances, even if a coating is provided on the master, some of the master may remain in recesses defined by the negative image. These remaining portions should be removed in order for the negative image to produce faithful replicates of the master. Thus an etching process, for example, KOH etching, may be performed to remove the layer of the material from the shell without damaging the underlying material, which in the embodiment described, is nickel.

Figure 4:
FIG. 4 is a negative image formed according to one embodiment of the invention.
Figure 5:
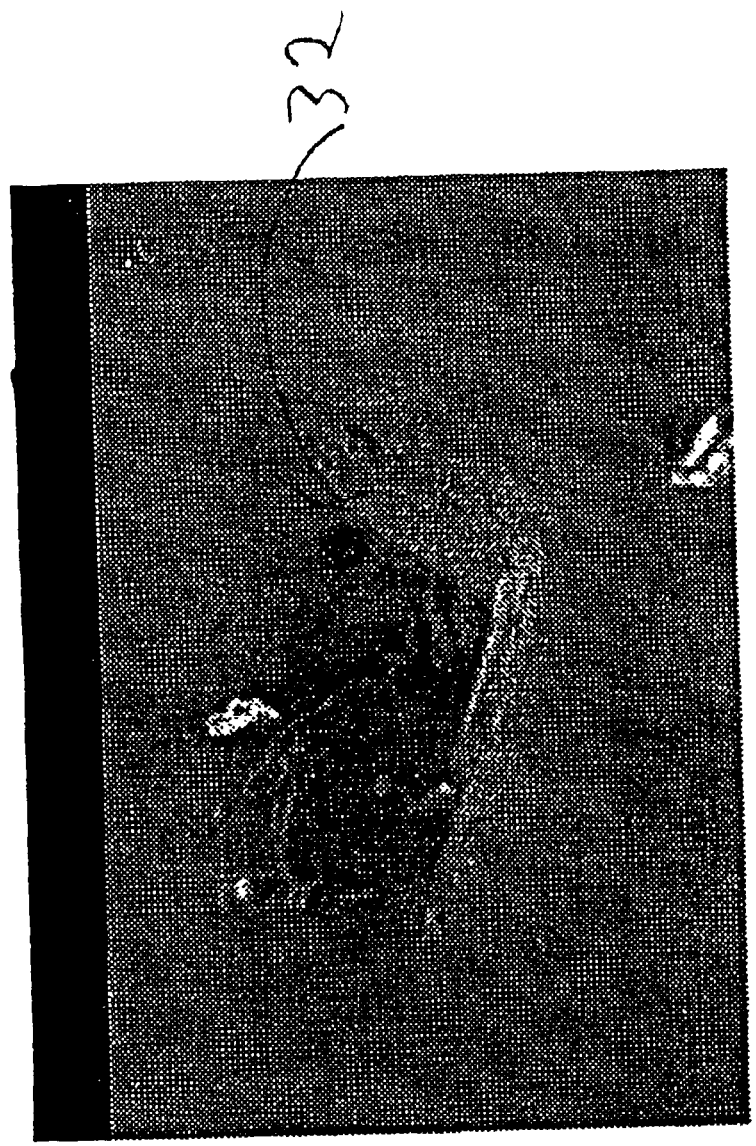
FIG. 5 is a magnified view of the negative image of FIG. 4.

An example of a shell 30 defining a negative image of an array of microprotrusions is shown in FIG. 4. The negative image in the shell 30 defines a cavity, i.e., a mold cavity. The mold cavity can be of any geometry or shape, as long as a master can be formed. A master used to form microabrader 10 as described above typically includes microprotrusions 14 spaced apart uniformly in rows and columns to form an array. Typically, the rows of microprotrusions are spaced in rows to provide a density of about 1 to about 10 per millimeter (mm) and provide a needle density of about 1 to about 100 needles per $mm^2$. Accordingly, the negative image includes an array of recesses 32 that correspond the microprotrusions 14 on the master microabrader 10. The recesses 32 have dimensions and a density corresponding to that of the microprotrusions 14 on the master. FIG. 5 is view of a single recess 32 for a microprotrusion which show the high quality of the negative image attained by the above-described process.

After the shell 30 is formed, it may undergo additional processing before it is used as a mold. Gate features, venting accesses, and sprue may be cut for the molding process. Additionally, modifications may be made to add geometry to the shell if desired. Features that are not present in the master, such as edge bevels, can also be added.

Figure 6:
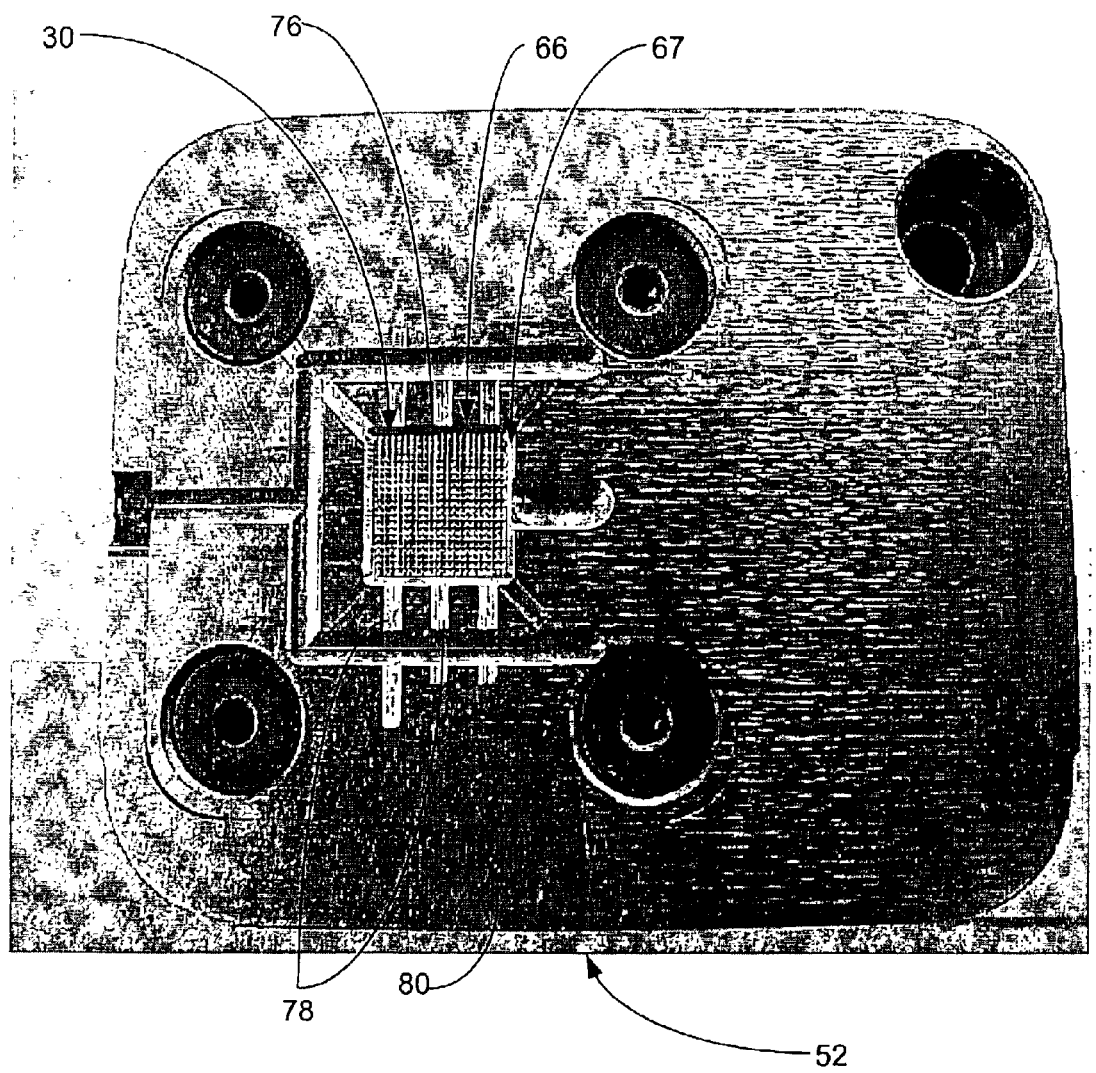
FIG. 6 is an exploded perspective view of a mold and mold member for molding a microprotrusion device.

After the shell is formed and processed, it can be used as a mold to form micro-devices, here microabraders, by injection molding. FIG. 6 shows a portion of a mold used during the injection molding process. Only one half of the mold is shown in FIG. 6, although another half of the mold is used during the molding process, as is well-known the one of ordinary skill in the art. As shown in FIG. 6, the shell 30 is attached to a mold section 52 in a recess 66 by a suitable coupling device or a heat resistant adhesive, such as an epoxy adhesive. In an alternative embodiment, a screw or other fastener is used to secure the shell 30 in place. The shell 30 placed against the surface of the mold section 52 and secured in place. Typically, the shell 30 is attached to a face of a bottom wall (not shown) of the recess 66. In further embodiments, the shell 30 can be attached to a side wall 67 of the recess. The shell 30 has a generally square shape complementing the shape of the recess 66 and generally extends between the side walls 67 of the recess 66 in the embodiment illustrated. In further embodiments, the shell 30 can have a dimension less than the dimension of the bottom wall. An upper face of the shell 30 defines a surface 76 for forming and shaping the micro-device. The surface 76 of the shell 30 is contoured in the form of an impression of the finished molded article. As described above, the surface 76 of the shell 30 can have at least one recess, ridge or peak having a width and/or height ranging from about 0.5 micron to about 500 microns depending on the device being molded. In the embodiment illustrated, the surface 76 of the shell has a plurality of recesses 32, as shown in FIG. 5, corresponding to the desired shape and dimensions of the microprotrusions for a microabrader device. When molding a microprotrusion device, the recesses can have a depth of about 5 to 250 microns and spaced to provide a density of about 1 to 100 recesses per $mm^2$. Accordingly, the surface 76 of the shell 30 is the reverse or impression of the molded micro-device. In one embodiment, the shell 30 has a thickness of about 0.01–0.2 inches thick and preferably about 0.07 inches or greater.

After being appropriately mounted in the molding apparatus, an injection molding process can be performed to make the micro-device, for example, the process described in U.S. Pat. No. 6,331,266 to Powell et al. During the injection molding process, the mold cavity is filled with a material, such as acrylic, COC, polyamides, polystyrenes, polyesters or polycarbonates as known in the art, to form the micro-device, i.e., microabrader. Either hot or cold runners may be used to during the injection molding process.

Due to the microstructure of the mold cavity, the recesses of mold cavity are not always completely filled during the injection molding process. Residual air can be present in the mold cavity, forming air bubbles and preventing the fill material from completely filling the recesses in the mold. The residual air in the mold cavity should be removed during injection molding in order to form the highest quality devices. Accordingly, the injection molding can be performed under vacuum to remove any residual air in the mold and to allow the polymer or other fill material to completely enter the recesses of the mold. Additionally, the tips of some or all of the peaks and recesses of the mold cavity may be provided with a vent to allow the residual air to escape or other venting procedures may be used to improve the filling of the recesses. The venting procedures may be used independent from or in conjunction with the vacuum processing.

FIG. 6 illustrates an example of a mold provided with vents. A surface 80 of mold section 52 is provided with a number of vents 78. Here, the mold section 52 is comprised of a metal and the vents 78 are very slight indentations in the surface 80. The vents may be formed by scraping away a very thin layer of the surface 80. The vents 80 should be sized such that residual air may escape from the recess 66, but the material used to fill the recess 66 does not substantially enter the vents 80.

The molded device can also be made using other molding processes. For example, a micro-device can be made by embossing a thermoplastic substrate with a mold or platen. The mold is provided with the impression of the desired molded micro-device. The device is formed by pressing the mold under pressure against the plastic substrate that has been heated to its softening temperature. Alternatively, the mold is heated and pressed against the thermoplastic substrate to mold the device.

In further embodiments, the device is formed by a compression molding method. In the compression molding method, a thermoplastic material, such as a powdered material, is placed in a hollow mold having a molding surface. The mold is closed and the powdered thermoplastic is compressed under high pressure and heated to melt and consolidate the powder particles. The molded device is then removed from the mold.

In another embodiment, the device is formed using a sintering process. In the sintering process, a powdered metallic material is placed in the hollow mold having the mold surface. The powdered metallic material substantially fills the hollow mold. Sintering is then performed to form a metallic device.

The microabrader formed according to the above processes above may have solid microprotrusions. A subsequent process, such as laser drilling, can be used to form hollow microprotrusions.

While several embodiments have been shown to illustrate the present invention, it will be understood by those skilled in the art that various changes and modifications can be made therein without departing from the scope of the invention as defined in the appended claims.

I claim:

1. A method of forming a mold for a micro-device including an array of microfeatures, comprising:
   providing a master having a surface contour which includes skin penetration features;
   covering the surface contour with a layer of material having a thickness of about 0.01–0.2 inches;
   removing the master from the layer of material to form a negative image of the master in the layer of material wherein the negative image is fillable by a flowable process;
   filling the negative image fluidically with a flowable powdered metallic materiel to form a device having substantially the same features as the master; and
   sintering the powdered metallic material to form the micro-device.

2. The method of claim 1, further comprising, coating the master with a release film, before the covering of the surface contour, to facilitate removal of the master.

3. The method of claim 1, further comprising, etching to remove the master.

4. The method of claim 3, wherein the etchant is hydroxide.

5. The method of claim 1, wherein the layer of material is a metal.

6. The method of claim 1, wherein the layer of material is nickel.

7. The method of claim 1, wherein the master is sacrificed during its removal.

8. The method of claim 1, Wherein the negative image has at least one structural feature of about 5 microns to about 250 microns in one dimension.

9. The method of claim 1, wherein the negative image defines recesses having a depth from its surface of about 5 microns to about 250 microns.

10. The method of claim 9, wherein the recesses are arranged in an array of uniformly spaced rows and columns to provide a density of about 1 to about 100 of the recess per mm2.

11. The method of claim 1, wherein the master is formed from silicon.

12. The method of claim 1, further comprising:
   individually forming portions of the master from silicon; and
   connecting the portions into a complete master.

13. The method of claim 1, wherein the layer of material is formed via sintering.

14. A method of forming a device including a plurality of micron or sub-micron sized features, the method comprising:
   providing a master having a surface contour defining skin penetration features;
   coating the surface contour of the master with at least one layer of material having a thickness of about 0.01–0.2 inches;
   removing the master from the layer of material to form a negative image of the surface contour in the layer of material;
   forming a mold insert from the negative image; and
   performing injection molding to fill the negative image fluidicaily to form a device having substantially the same features as the master.

15. The method of claim 14, wherein the injection molding is done at a vacuum.

16. The method of claim 14, further comprising drilling holes in the features of the device to form hollow microneedles.

17. The method of claim 14, wherein the layer of material is at about 0.07 inches thick.

18. The method of claim 14, further comprising, coating the master with a release film, before the covering of the surface contour, to facilitate removal of the master.

19. The method of claim 14, further comprising, etching to remove the master.

20. The method of claim 14, wherein the layer of material is a metal.

21. The method of claim 14, wherein the layer of material is nickel.

22. The method of claim 14, further comprising removing residual air during the injection molding.

23. The method of claim 14, further comprising forming vents in the mald insert.

24. The method of claim 14, wherein the negative image is filled with a polymer.

25. The method of claim 14, wherein the negative image is filled with one of polyethylene, polypropylene, acrylic, cyclic olefinic copolymers, polyamide, polystyrene, polyester and polycarbonate.

26. The method of claim 16, wherein the drilling is performed via lasers.

27. The method of claim 14, wherein the layer of material is formed via sintering.

28. The method of claim 14, wherein the filling step further comprises:
   filling the negative image with a flowable powdered metallic material; and
   sintering the powdered metallic material to form the micro-device.

29. The method of claim 14, wherein the master is formed from silicon.

30. The method of claim 29, further comprising:

individually forming portions of the master from silicon; and connecting the portions into a complete master.

31. A method of forming a device including a plurality of micron or sub-micron sized features, the method comprising:

providing a master having a surface contour defining features;

coating the surface contour of the master with at least one layer of material at about 0.07 inches thick;

removing the master from the layer of material to form a negative image of the surface contour in the layer of material; and filling the negative image to form a device having substantially the same features as the master.

32. The method claim 31, further comprising, forming a mold insert from the negative image; and performing injection molding to fill the negative image.

33. The method of claim 32, wherein the injection molding is done at a vacuum.

34. The method of claim 31, wherein the negative image is filled with a polymer.

35. The method of claim 34, wherein the negative image is filled with one of polyethylene, polypropylene acrylic, cyclic olefinic copolymers, polyamide, polystyrenes, polyester and polycarbonate.

36. A method of forming a medical device including a plurality of micron or sub-micron sized features which form skin penetration members, the method comprising:

providing a master having a surface contour defining skin penetration features;

coating the surface contour of the master with a single layer of material having a thickness of about 0.01–0.2 inches;

removing the master from the layer of material to form a negative image of the surface contour in the layer of material forming a mold insert from the negative image; and performing injection molding to fill the negative image fluidically to form the medical device having substantially the same features as the master.

37. The method of claim 36, wherein the injection molding is done at a vacuum.

38. The method of claim 36, wherein the negative image is filled with a polymer.

39. The method of claim 38, wherein the negative image is filled with one of polyethylene, polypropylene, acrylic, cyclic olefinic copolymers, polyamide, polystyrenes, polyester and polycarbonate.

* * * * *